(12) United States Patent
Miyahara et al.

(10) Patent No.: US 7,096,058 B2
(45) Date of Patent: Aug. 22, 2006

(54) LASER BLOOD-FLOW METER AND SYSTEM FOR MONITORING BIO-DATA

(75) Inventors: Takaaki Miyahara, Tokyo (JP); Kazuto Mishima, Tokyo (JP); Jun Niwayama, Tokyo (JP); Tomiko Yanagi, Tokyo (JP)

(73) Assignee: Cyberfirm Inc., Tokyo (JP)

( * ) Notice: Subject to any disclaimer, the term of this patent is extended or adjusted under 35 U.S.C. 154(b) by 0 days.

(21) Appl. No.: 10/857,894

(22) Filed: Jun. 2, 2004

(65) Prior Publication Data

US 2004/0254473 A1    Dec. 16, 2004

(30) Foreign Application Priority Data

Jun. 2, 2003   (JP) ............................ 2003-156943

(51) Int. Cl.
   *A61B 6/00*   (2006.01)
(52) U.S. Cl. .................. 600/476; 600/473; 600/479; 600/483; 250/557; 604/29; 385/33; 359/652
(58) Field of Classification Search ............... 600/473, 600/476, 479, 483; 250/557; 604/29; 385/33; 359/652
   See application file for complete search history.

(56) References Cited

U.S. PATENT DOCUMENTS

| 4,557,566 | A | * | 12/1985 | Kikuchi et al. | ............. | 359/652 |
| 5,743,267 | A | * | 4/1998 | Nikolic et al. | ............. | 600/483 |
| 5,778,878 | A | * | 7/1998 | Kellam | ............. | 600/473 |
| 6,223,069 | B1 | | 4/2001 | Pfeiffer et al. | | |
| 6,580,086 | B1 | * | 6/2003 | Schulz et al. | ............. | 250/557 |
| 6,876,790 | B1 | * | 4/2005 | Lee | ............. | 385/33 |
| 2002/0120203 | A1 | | 8/2002 | Higurashi et al. | | |
| 2002/0188205 | A1 | | 12/2002 | Mills | | |
| 2003/0220606 | A1 | * | 11/2003 | Busby et al. | ............. | 604/29 |

FOREIGN PATENT DOCUMENTS

| DE | 100 33 171 A1 | 1/2002 |
| EP | 0 282 210 A1 | 9/1988 |
| EP | 0 771 546 A2 | 5/1997 |
| JP | 57-134658 | 8/1982 |
| JP | 58-185203 | 12/1983 |
| JP | 1-256924 | 10/1989 |
| JP | 2-203838 | 8/1990 |
| JP | 10-165381 | 6/1998 |
| JP | 2001-120509 | 5/2001 |
| JP | 2002-45342 | 2/2002 |
| JP | 37-31395 | 1/2006 |
| WO | WO 85/03211 | 8/1985 |

OTHER PUBLICATIONS

European Search Report dated Dec. 23, 2004.

* cited by examiner

*Primary Examiner*—Brian L. Casler
*Assistant Examiner*—Baisakhi Roy
(74) *Attorney, Agent, or Firm*—McGinn IP Law Group, PLLC

(57) ABSTRACT

A laser blood-flow meter includes a laser-beam irradiator for irradiating laser beams to biological structure, a detector for detecting scattered beams resulted from scattering of the laser beams in the biological structure, the laser blood-flow meter measuring blood flow of the biological structure in accordance with the scattered beams detected by the detector, and a beam-collector for collecting the scattered beams to direct the collected beams to the detector.

15 Claims, 9 Drawing Sheets

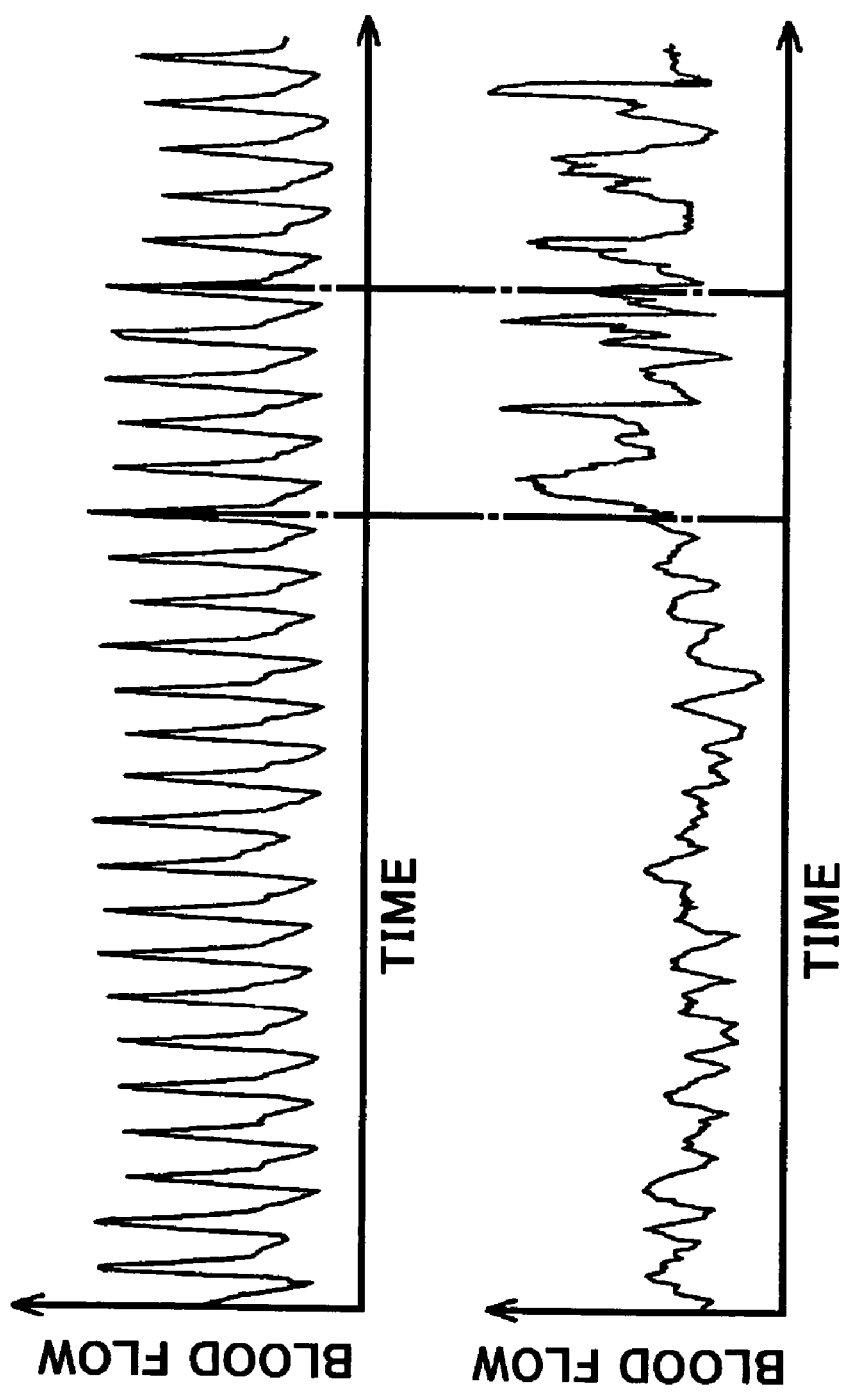

LASER BLOOD-FLOW METER AND SYSTEM FOR MONITORING BIO-DATA

BACKGROUND OF THE INVENTION

1. Field of the Invention

The invention relates to a laser blood-flow meter and a system for monitoring bio-data.

2. Description of the Related Art

Japanese Patent Application Publication No. 2002-45342 has suggested a laser blood-flow meter which irradiates laser beams to biological structure to allow the laser beams to be scattered in the biological structure, and detect power spectrum of scattered laser beams to thereby measure blood flow in the biological structure.

The suggested laser blood-flow meter measures or calculates blood flow by virtue of a speckle interference process making use of diffraction of laser beams scattered in biological structure.

Herein, speckle interference indicates, with respect to measurement of blood flow, a spotted noise or interference pattern obtained when scattered beam resulted when laser beams irradiated to biological structure are scattered with erythrocytes in blood are observed at a facet. The noise or interference pattern varies in accordance with movement of erythrocytes.

A laser blood-flow meter operates in accordance with such a principle as mentioned above. A laser blood-flow meter detects an interference pattern by irradiating laser beams to biological structure such that the interference pattern appears on a detection screen of a detector such as a photodiode, and measures blood flow, based on correlation between variance in the interference pattern and movement of erythrocytes.

Measurement of blood flow in a laser blood-flow meter is made with a sensor of the laser blood-flow meter being attached to a person to be monitored. Accordingly, when blood flow is measured continuously for a long time, a laser blood-flow meter would receive artifact noises caused by the person's slight movement and/or measurement environment.

The artifact noises often become extremely high in proportion with power spectrum of scattered beams, in which case, it is not possible to properly measure blood flow.

Thus, it was difficult or almost impossible to properly measure blood flow by applying a laser blood-flow meter to a monitor system which was necessary to receive for a long time blood flow data and biological data having correlation with the blood flow.

It is empirically known that blood flow in a head is different from blood flow in quarters. Hence, it has been said that blood flow in a head and quarters were necessary to be measured independently of each other, but it was not possible to do so because of the above-mentioned artifact noises.

Japanese Patent Application Publication No. 2001-120509 has suggested an apparatus for detecting power spectrum as a blood-flow signal, including a laser-beam source emitting laser beams in a longitudinal single mode, first means for stabilizing a wavelength of the laser beams, and second means for converting laser beams reflected from an object, into electric signals.

Japanese Patent Application Publication No. 1-256924 has suggested a method of diagnosing eyes including the step of irradiating laser beams to eyes wherein laser beams are received by a beam receiver through an optical fiber, a lens being disposed between the beam receiver and the optical fiber.

Japanese Utility Model Publication No. 37-31395 has suggested a lumen mirror including a beam irradiator, a beam collector and a detector.

Japanese Patent Application Publication No. 2-203838 has disclosed a probe for measuring blood flow, as prior art, including a prism for turning laser beams by 90 degrees.

Japanese Utility Model Publication No. 57-134658 has suggested a device for detecting whether a droplet exists on an object, including a beam block which prevents a beam irradiated from a beam emitter, from being directly received at a beam receiver.

Japanese Utility Model Publication No. 58-185203 has suggested an optical fiber sensor used for forward-scattered beams.

SUMMARY OF THE INVENTION

In view of the above-mentioned problem, it is an object of the present invention to provide a laser blood-flow meter and a system for monitoring bio-data both of which are capable of being less influenced by artifact noises, and readily and stably measuring blood flow in a head and quarters independently of each other.

Hereinbelow are described a laser blood-flow meter and a system for monitoring bio-data both in accordance with the present invention through the use of reference numerals used in later described embodiments. The reference numerals are indicated only for the purpose of clearly showing correspondence between claims and the embodiments. It should be noted that the reference numerals are not allowed to use in the interpretation of claims of the present application.

In one aspect of the present invention, there is provided a laser blood-flow meter including a laser-beam irradiator (12) for irradiating laser beams (L) to biological structure (11), a detector (13) for detecting scattered beams (S) resulted from scattering of the laser beams (L) in the biological structure (11), the laser blood-flow meter measuring blood flow of the biological structure (11) in accordance with the scattered beams (S) detected by the detector (13), and a beam-collector (15) for collecting the scattered beams (S) to direct the collected beams to the detector (13).

Since the laser blood-flow meter in accordance with the present invention includes the beam-collector, it would be possible to collect scattered beams, and amplify signals necessary for measurement of blood flow. That is, it would be possible to reduce artifact noises relatively to the signals, and hence, the laser blood-flow meter could be less influenced by artifact noises. Thus, it is now possible to solve the problem that blood flow cannot be properly measured because of artifact noises. Hence, it is also possible to apply the laser blood-flow meter in accordance with the present invention to a monitor system which is necessary to receive for a long time blood flow data and biological data having correlation with the blood flow. Furthermore, the laser blood-flow meter in accordance with the present invention can readily and stably measure blood flow in a head and quarters independently of each other The detector (13) and the laser-beam irradiator (12) may be disposed on a common side relative to the biological structure (11) such that the detector (13) detects backward-scattered beams (S).

The laser blood-flow meter may further include a case (110a) in which the laser-beam irradiator (12), the beam-collector (15) and the detector (13) are arranged, in which case, it is preferable that the case (110a) has a flat contact-surface (101), as at least a part of an external surface thereof, at which the case (110a) makes contact with a surface of the biological structure (11) when blood flow of the biological structure (11) is measured, and the laser-beam irradiator (12), the beam-collector (15) and the detector (13) are arranged in this order on a path substantially parallel with the flat contact-surface (101). Thus, it is possible to render the contact-surface more stable, ensuring that the laser blood-flow meter is less influenced by artifact noises during measurement of blood flow.

The laser blood-flow meter may further include a light-guide (17) arranged between the detector (13) and the beam-collector (15) for guiding beams collected by the beam-collector (15) to the detector (13).

The laser blood-flow meter may further include a first beam-turner (14) for turning the laser beams (L) irradiated from the laser-beam irradiator (12) towards the biological structure (11), and a second beam-turner (16) for turning the scattered beams (S) towards the beam-collector (15).

It is preferable that the contact-surface (101) has a beam-transmissive portion (18) through which the laser beams (L) can transmit, and the laser blood-flow meter further includes a beam-block (19) which prevents laser beams (L) having passed through the beam-transmissive portion (18) from being directed towards the second beam-turner (16) and the beam-collector (15) without reaching the biological structure (11).

It is preferable that the detector (13) and the laser-beam irradiator (12) are disposed on opposite sides to each other relative to the biological structure (11) such that the detector (13) detects forward-scattered beams (S).

For instance, the beam-collector (15) may be comprised of a semispherical lens.

For instance, the light-guide (17) may be comprised of one of a pin-hole, an optic fiber and a bar lens.

It is preferable that the beam-block (19) projects outwardly over the beam-transmissive portion (18).

There is further provided a laser blood-flow meter including a laser-beam irradiator (12) for irradiating laser beams (L) to biological structure (11), a detector (13) for detecting scattered beams (S) resulted from backward-scattering of the laser beams (L) in the biological structure (11), the laser blood-flow meter measuring blood flow of the biological structure (11) in accordance with the scattered beams (S) detected by the detector (13), a light-guide (17) for guiding the scattered beams (S) to the detector (13), and a case (110a) in which the laser-beam irradiator (12), the light-guide (17) and the detector (13) are arranged, wherein the case (110a) has a flat contact-surface (101), as at least a part of an external surface thereof, at which the case (110a) makes contact with a surface of the biological structure (11) when blood flow of the biological structure (11) is measured, and the laser-beam irradiator (12), the light-guide (17) and the detector (13) are arranged in this order on a path substantially parallel with the flat contact-surface (101).

The laser blood-flow meter may further include a first beam-turner (14) for turning the laser beams (L) irradiated from the laser-beam irradiator (12) towards the biological structure (11), and a second beam-turner (16) for turning the scattered beams (S) towards the light-guide (17).

There is still further provided a laser blood-flow meter including a laser-beam irradiator (12) for irradiating laser beams (L) to biological structure (11), and a detector (13) for detecting scattered beams (S) resulted from scattering of the laser beams (L) in the biological structure (11), the laser blood-flow meter measuring blood flow of the biological structure (11) in accordance with the scattered beams (S) detected by the detector (13), wherein the detector (13) and the laser-beam irradiator (12) are disposed on opposite sides to each other relative to the biological structure (11) such that the detector (13) detects forward-scattered beams (S).

The laser blood-flow meter may further include a clip (21) for clipping the laser blood-flow meter to the biological structure (11), the clip (21) including a first portion (21a) in which the laser-beam irradiator (12) is arranged, and a second portion (21b) in which the detector (13) is arranged.

The laser blood-flow meter may further include a hinge (22) through which the first and second portions (21a, 21b) are swingable to each other.

The laser blood-flow meter may further include a phase-converter (23) providing a first phase in which the first and second portions (21a, 21b) sandwich the biological structure (11) therebetween such that the laser blood-flow meter is attached to the biological structure (11), and a second phase in which the first and second portion (21a, 21b) are open to each other such that the laser blood-flow meter is released from the biological structure (11).

The laser blood-flow meter may further include a beam-collector (15) for collecting the scattered beams (S) to direct the collected beams to the detector (13).

In another aspect of the present invention, there is provided a system for monitoring bio-data of biological structure (11), including a laser blood-flow meter measuring blood flow of the biological structure (11) in accordance with scattered beams (S) resulted from scattering of laser beams (L) in the biological structure (11) which laser beams (L) have been irradiated to the biological structure (11), the system monitoring the bio-data, based on blood flow in a head (31a) of the biological structure (11) and blood flow in any one of quarters (31b) of the biological structure (11), the system including a controller (42) which judges whether a blood flow and a blood-flow waveform of a head (31a) of the biological structure (11) are in synchronization with a blood flow and a blood-flow waveform of any one of quarters (31b) of the biological structure (11), and does not use a blood flow and a blood-flow waveform obtained when the blood flow and the blood-flow waveform of the head (31a) is not in synchronization with the blood flow and the blood-flow waveform of the any one of quarters (31b), for monitoring the bio-data.

In accordance with the above-mentioned system, blood flow and a blood-flow waveform obtained when the blood flow and the blood-flow waveform of the head is not in synchronization with the blood flow and the blood-flow waveform of the any one of quarters are not used for monitoring bio-data, ensuring that bio-data is monitored based on blood flow and a blood-flow waveform both having been properly measured. That is, blood flow and a blood-flow waveform both much influenced by artifact noises are not used for monitoring bio-data, and accordingly, it is ensured that the laser blood-flow meter is less influenced by artifact noises. Furthermore, when blood flow and a blood-flow waveform of a head and quarters are measured independently of each other, it would be possible to readily and stably do so.

It is preferable that the controller (42) compares the measured blood flow and blood-flow waveform to a reference blood flow and a reference blood-flow waveform, respectively, to judge whether the measured blood flow and blood-flow waveform are properly measured, and wherein a blood flow and a blood-flow waveform having been judged not to be properly measured are not used for monitoring the bio-data.

It is preferable that the controller (42) judges whether a person (31) to be monitored is in a serious condition.

It is preferable that the controller (42) compares the measured blood flow and blood-flow waveform to a reference blood flow and a reference blood-flow waveform, respectively, to judge whether a person (31) to be monitored is in a serious condition.

It is preferable that the system further includes an annunciator which makes annunciation when the controller (42) judges that the person (31) is in a serious condition.

It is preferable that the system monitors the bio-data while blood is circulated between a person (31) and an external device (50).

It is preferable that the system further includes an artificial dialysis device (50) for carrying out artificial dialysis, and wherein the system monitors the bio-data of a person (31) while dialysis is carried out to the person (31) by the artificial dialysis device (50).

As a laser blood-flow meter, there may be used the above-mentioned one.

The advantages obtained by the aforementioned present invention will be described hereinbelow.

In accordance with the present invention, it is possible to reduce harmful influence caused by artifact noises, and readily and stably measure blood flow of a head and quarters independently of each other continuously for a long time.

The above and other objects and advantageous features of the present invention will be made apparent from the following description made with reference to the accompanying drawings, in which like reference characters designate the same or similar parts throughout the drawings.

BRIEF DESCRIPTION OF THE DRAWINGS

FIGS. 9A and 9B illustrate blood-flow waveforms not in synchronization with each other.

DESCRIPTION OF THE PREFERRED EMBODIMENTS

Preferred embodiments in accordance with the present invention will be explained hereinbelow with reference to drawings.

First Embodiment

Figure 1:
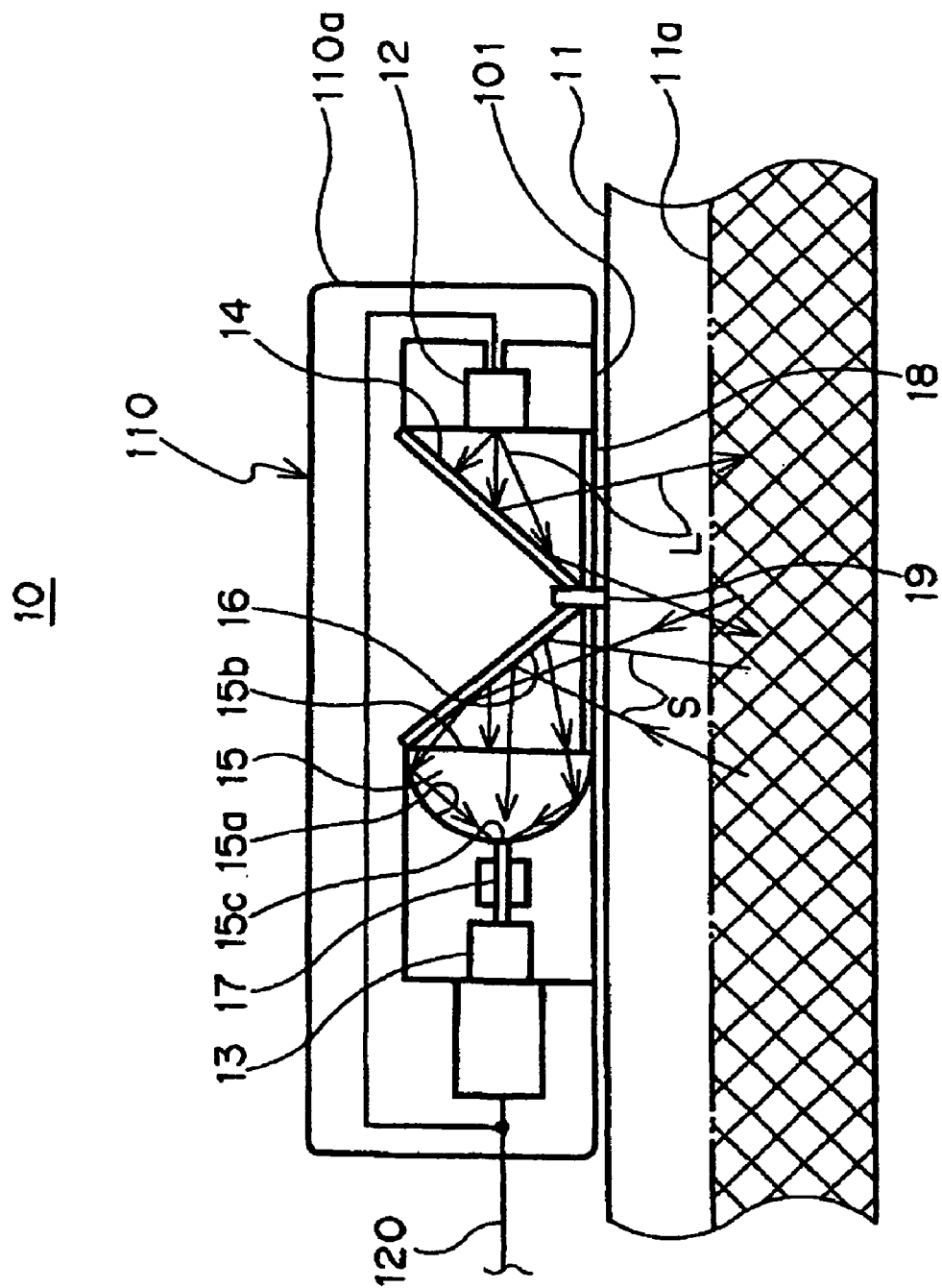
FIG. 1 is a cross-sectional view of the laser blood-flow meter in accordance with the first embodiment of the present invention.
Figure 2:
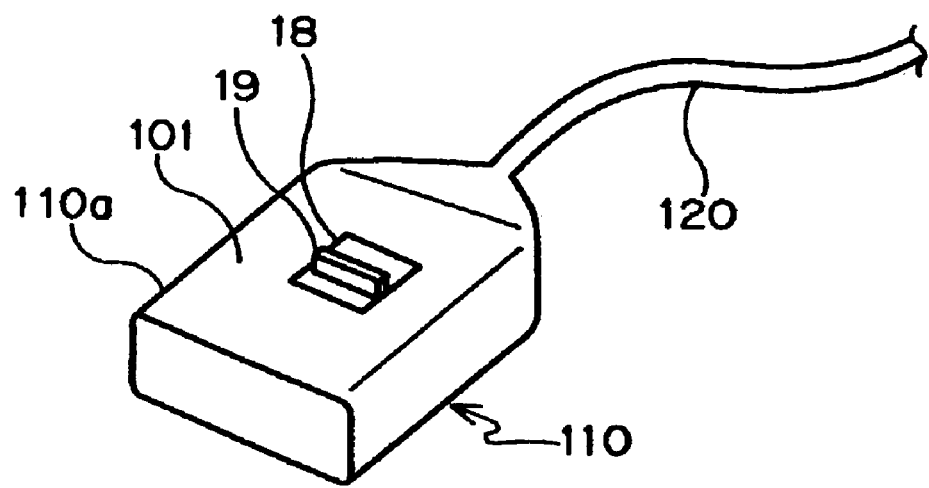
FIG. 2 is a perspective view of the laser blood-flow meter in accordance with the first embodiment of the present invention.

The laser blood-flow meter in accordance with the first embodiment is of a backward-scattered type. Hereinbelow is explained the laser blood-flow meter in accordance with the first embodiment with reference to FIGS. 1 and 2, wherein FIG. 1 is a cross-sectional view of the laser blood-flow meter, and FIG. 2 is a perspective view of the laser blood-flow meter. A later-mentioned contact surface 101 faces downwardly in FIG. 1, whereas the same faces upwardly in FIG. 2.

As illustrated in FIG. 1, the laser blood-flow meter 10 in accordance with the first embodiment is comprised of a laser-beam irradiator 12 for irradiating laser beams L to biological structure 11, a detector 13 for detecting scattered beams S resulted from scattering of the laser beams L in the biological structure 11, and an operation unit (not illustrated) which measures or calculates blood flow of the biological structure 11 in accordance with power spectrum of the scattered beams S detected by the detector 13.

The detector 13 is comprised of a photodiode.

In FIG. 1, reference signs L and S are given only to a part of the laser beams and scattered beams.

In the laser blood-flow meter 10, the detector 13 and the laser-beam irradiator 12 are disposed on a common side relative to the biological structure 11 such that the detector 13 detects backward-scattered beams S. That is, the laser blood-flow meter 10 is a backward-scattered type laser blood-flow meter.

The laser blood-flow meter 10 is comprised of a sensor unit 110 and a controller (not illustrated) including the operation unit therein. The sensor unit 110 includes the laser-beam irradiator 12, the detector 13 and later-mentioned parts all arranged in a unit.

The controller and the sensor unit 110 are electrically connected to each other through a signal line 120. The detector 13 in the sensor unit 110 transmits a detection signal to the controller through the signal line 120, and the controller transmits a command signal to the laser-beam irradiator 12 through the signal line 120.

The laser-beam irradiator 12 is comprised of a laser diode, for instance. The laser-beam irradiator 12 irradiates laser beams L in a longitudinal single mode, having a wavelength in the range of 500 to 900 micrometers both inclusive, for instance. The laser-beam irradiator 12 is disposed such that it irradiates the laser beams L along a surface of the biological structure 11 when blood flow is measured.

Thus, the sensor unit 110 is designed to include a first light-reflector 14 as a first beam-turner for reflecting the laser beams L towards the biological structure 11. The first light-reflector 14 has a reflection surface inclining about 45 degrees, for instance, relative to a direction in which the laser beams L are irradiated from the laser-beam irradiator 12.

The sensor unit 110 is designed to further include a beam-collector for collecting the scattered beams S and directing the collected beams to the detector 13. The beam-collector is comprised of a semispherical lens 15 in the first embodiment. The semispherical lens 15 has a diameter in the range of 1 to 6 millimeters both inclusive, for instance.

The semispherical lens 15 is comprised of a semispherical portion 15a directing towards the detector 13 and a planar portion 15b directing towards the laser-beam irradiator 12.

Furthermore, the semispherical lens 15 has a central axis substantially coincident with a direction in which the laser beams L are irradiated from the laser-beam irradiator 12.

The semispherical portion 15a is formed at a summit thereof with a laser-beam outlet 15c. The semispherical portion 15a is coated at an inner surface thereof with a light-reflective film except the laser-beam outlet 15c.

Accordingly, the scattered beams S introduced into the semispherical portion 15a through the planar portion 15b are reflected at the light-reflective film to converge to the laser-beam outlet 15c. The thus converged scattered beams S are introduced into a later-mentioned a pin-hole 17 as a light-guide through the laser-beam outlet 15c.

The laser-beam outlet 15c has a diameter in the range of 50 to 100 micrometers both inclusive, for instance, in accordance with a diameter of the pin-hole 17.

The sensor unit 110 is designed to further include a second light-reflector 16 as a second beam-turner for reflecting the scattered beams S towards the semispherical lens 15 from the biological structure 11. The second light-reflector 16 has a reflection surface inclining about 45 degrees, for instance, relative to a central axis of the semispherical lens 15.

The first and second light-reflectors 14 and 16 are rectangular in shape, for instance. They are arranged almost perpendicularly to each other and make contact with each other at one side which faces the biological structure 11 when blood flow is measured.

Because of the second light-reflector 16, the semispherical lens 15 collects not only the scattered beams S directly arriving from the biological structure 11, but also the scattered beams S reflected at the second light-reflector 16.

The sensor unit 110 is designed to include a pin-hole 17 as a light-guide for guiding the scattered beams S collected by the semispherical lens 15 to the detector 13. The pin-hole 17 as a light-guide is arranged between the detector 13 and the semispherical lens 15.

The pin-hole 17 has a diameter in the range of 50 to 100 micrometers both inclusive, for instance, in accordance with a size of the laser-beam outlet 15c.

The sensor unit 110 includes a case 110a pin which the laser-beam irradiator 12, the first and second light-reflectors 14 and 16, the semispherical lens 15, the pin-hole 17, and the detector 13 are arranged.

The case 110a has a flat contact-surface 101 as at least a part of an external surface of the case 110a. The case 110a makes contact with a surface of the biological structure 11 through the flat contact-surface 101 when blood flow of the biological structure 11 is measured. Hence, the sensor unit 110 can make stable contact with a surface of the biological structure 11 when blood flow of the biological structure 11 is measured.

The laser-beam irradiator 12, the semispherical lens 15, the pin-hole 17 and the detector 13 are arranged in this order on a linear path (for instance, a central axis of the semispherical lens 15) substantially parallel with the flat contact-surface 101.

Since the laser-beam irradiator 12, the semispherical lens 15, the pin-hole 17 and the detector 13 are disposed along the contact-surface 101, the arrangement which enables the sensor unit 110 to make stable contact with a surface of the biological structure 11 is efficiently accomplished.

As illustrated in FIGS. 1 and 2, the contact-surface 101 is designed to have a glass plate 18 as a beam-transmissive portion through which the laser beams can transmit. For instance, a transparent resin plate may be used in place of the glass plate 18. Any plate may be used as the beam-transmissive portion, if it is composed of a material through which the laser beams L can transmit.

The glass plate 18 acts as a protector for protecting the laser-beam irradiator 12, the first and second light-reflectors 14 and 16, and the semispherical lens 15 from external impact, and accomplishes transmission of the laser beams L to the biological structure 11 from the first light-reflector 14 and transmission of the scattered beams S to the second light-reflector 16 and the semispherical lens 15 from the biological structure 11.

The laser beams L may disadvantageously repeat reflection between the glass plate 18 and a surface of the biological structure 11 without reaching interior of the biological structure 11, and reach the second light-reflector 16 and the semispherical lens 15.

In order to avoid such a problem, the sensor unit 110 is designed to include a beam-block 19. As illustrated in FIGS. 1 and 2, the beam-block 19 extends through the glass plate 18 and projects outwardly beyond the case 110a. The beam block 19 is compressed onto a surface of the biological structure 11 when blood flow is measured.

The beam-block 19 removes the laser beams L repeating reflection between the glass plate 18 and a surface of the biological structure 11. Accordingly, the semispherical lens 15 collects only the scattered beams S returning back from the biological structure 11.

The laser blood-flow meter 10 has such a structure as mentioned above.

The semispherical lens 15 as a beam-collector, the pin-hole 17 as a light-guide, and the detector 13 (photodiode) constitutes a transducer unit.

Hereinbelow is explained an operation of the laser blood-flow meter 10.

First, the sensor unit 110 of the laser blood-flow meter 10 is set on a surface of the biological structure 11 such as a man such that the contact-surface 101 including the glass plate 18 makes contact with a surface of the biological structure 11. The sensor unit 110 may be fixed onto a surface of the biological structure 11 by means of a band, for instance.

Then, the laser-beam irradiator 12 irradiates the laser beams L under control by the controller. The irradiated laser beams L are reflected at the first light-reflector 14, and then, enters the biological structure 11 through the glass plate 18.

There are generated scattered beams S as a result of scattering of the laser beams L in the biological structure 11. A part of the scattered beams S is backwardly scattered towards the sensor unit 110 from the biological structure 11. The backwardly scattered beams S enter directly into the semispherical lens 15 through the glass plate 18, or enter the semispherical lens 15 after reflected at the second light-reflector 16.

Since the laser beams repeating reflection between the glass plate 18 and the biological structure 11 are removed by the beam-block 19, only the scattered beams S (backwardly scattered beams) returning back from the biological structure 11 are collected by the semispherical lens 15.

The scattered beams S having been collected by the semispherical lens 15 are detected by the detector 13 through the pin-hole 17.

Due to the Doppler shift phenomenon caused by speckle interference, an interference pattern of the scattered beams S appears on a detection screen of the detector 13. The interference pattern is detected by the detector 13. Since the interference pattern varies in accordance with movement of erythrocytes, it is possible to measure blood flow in the biological structure 11 in accordance with variance in the interference pattern.

That is, scattered beams resulted from movement of erythrocytes among the backwardly scattered beams S are converted into an alternating current (AC), and the detector 13 measures blood flow by detecting the alternating current.

Figure 3:
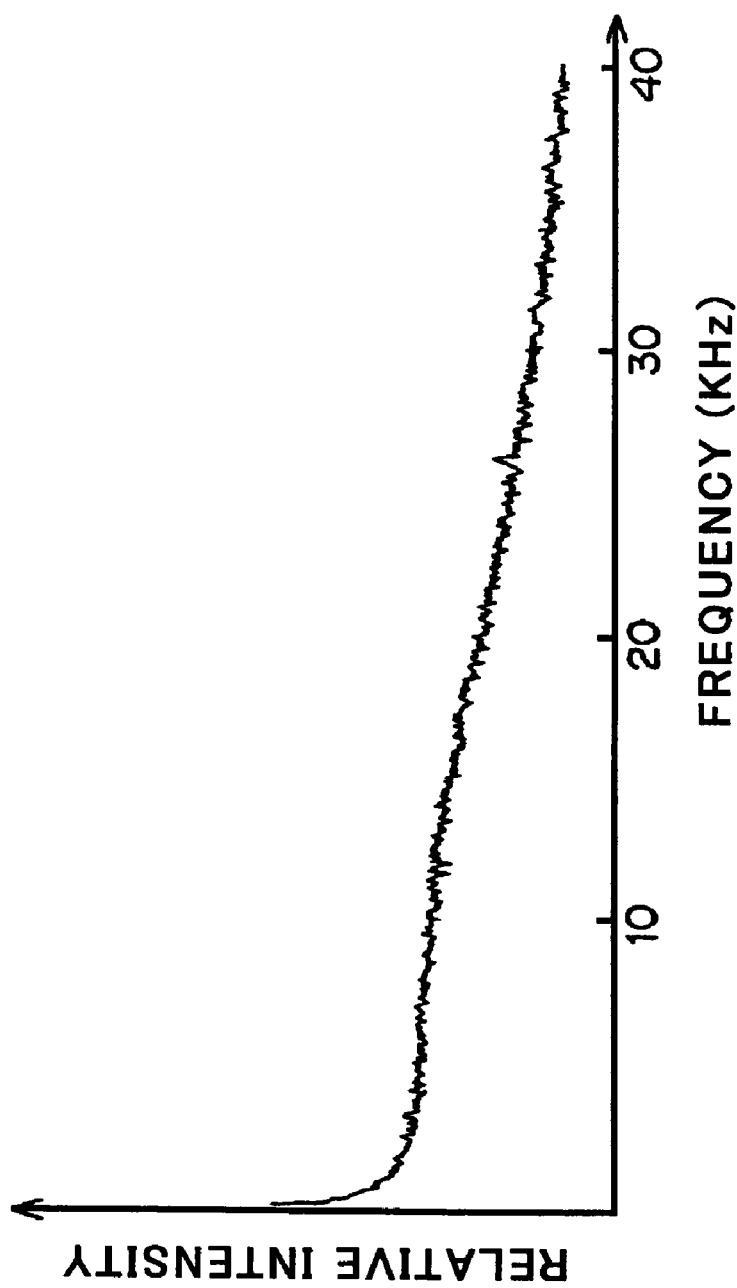
FIG. 3 illustrates power spectrum of scattered beams detected by the laser blood-flow meter in accordance with the first embodiment.
Figure 4:
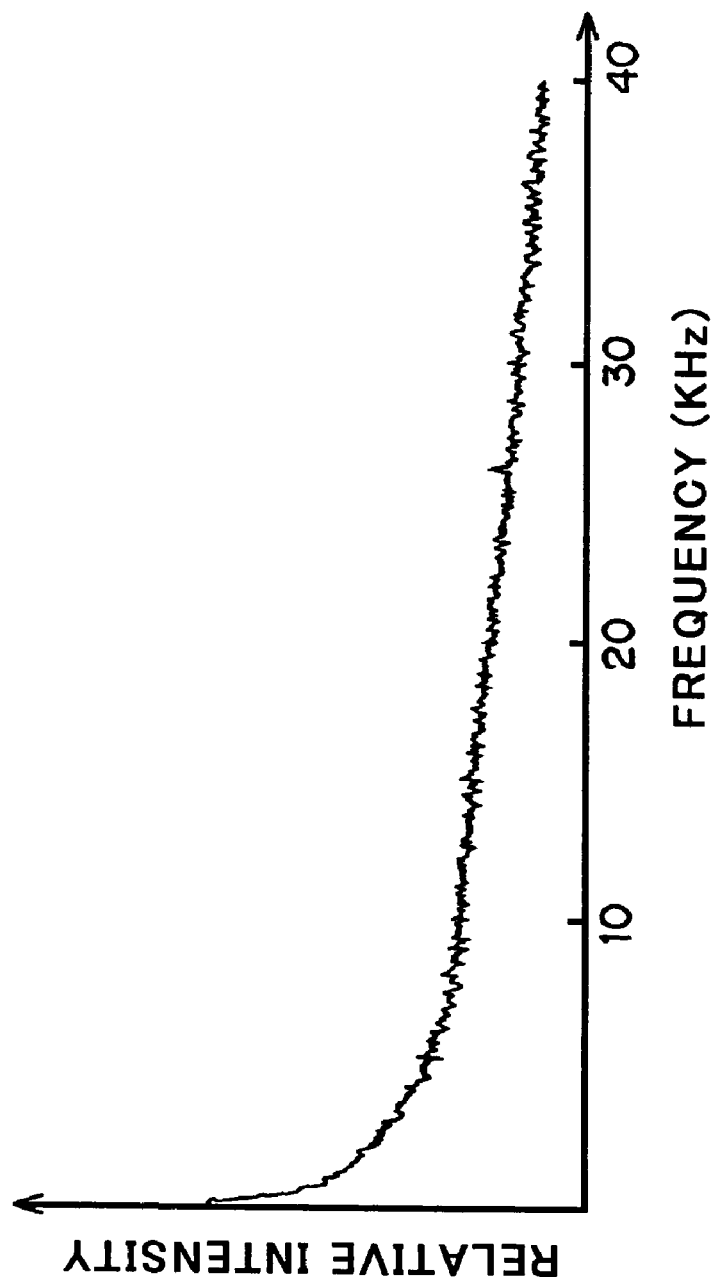
FIG. 4 illustrates power spectrum of scattered beams detected by a conventional laser blood-flow meter.

FIG. 3 illustrates power spectrum equivalent to the detected alternating current, whereas FIG. 4 illustrates power spectrum detected by a conventional laser blood-flow meter.

As is obvious in comparison between FIGS. 3 and 4, the laser blood-flow meter 10 in accordance with the first embodiment provides enhanced power spectrum in comparison with the conventional laser blood-flow meter.

This is because the laser blood-flow meter 10 in accordance with the first embodiment is designed to include the semispherical lens 15 which collects the scattered beams S, that is, spatially integrates the scattered beams S, and hence, provides a broader range in which blood flow is measured.

Scattered beams resulted from stationary biological structure and/or stationary erythrocytes among the backwardly scattered beams S are converted into a direct current (DC).

Relation among the above-mentioned scattered beams is defined in accordance with the following equation (I).

$$P=F(w)+N(w)+I(t) \qquad (I)$$

P: Power spectrum

F(w): Power at an average frequency of scattered beams resulted from moving erythrocytes N(w): Power resulted from noises in a laser-beam source and quantum noises of a photoelectric converter I(t): Volume of scattered beams resulted from stationary biological structure and/or stationary erythrocytes As illustrated in FIG. 1, artery and vein are disposed in a blood vessel area 11a located deep from a surface of the biological structure 11. Hence, only the scattered beams S resulted from that the laser beams L reaching the blood vessel area 11a are backwardly scattered by erythrocytes in the blood vessel area 11a contribute to F(w).

Since the laser blood-flow meter 10 in accordance with the first embodiment includes the semispherical lens 15 as a beam-collector, it is possible to collect the scattered beams S, and increase F(w), namely, signals necessary for measuring blood flow. In other words, it is possible to reduce artifact noises relative to signals F(w), and hence, the laser blood-flow meter 10 can be less influenced by artifact noises.

Furthermore, collection of the scattered beams S by means of the semispherical lens 15 would provide a broader range in which blood flow is measured in the biological structure 11.

The laser blood-flow meter 10 is designed to include the case 110a in which the laser-beam irradiator 12, the first and second light-reflectors 14 and 16, the semispherical lens 15, the pin-hole 17, and the detector 13 are arranged. The case 110a is designed to have a flat contact-surface 101 as at least a part of an external surface of the case 110a. The case 110a makes contact with a surface of the biological structure 11 through the flat contact-surface 101 when blood flow of the biological structure 11 is measured. In addition, the laser-beam irradiator 12, the semispherical lens 15, the pin-hole 17 and the detector 13 are arranged in this order on a linear path substantially parallel with the flat contact-surface 101. Hence, it is possible to make the contact-surface 101 broader and more stable without increasing a size of the sensor unit 110. Thus, the sensor unit 110 can be readily attached to a target, and be less influenced by noises caused by oscillation.

As is obvious in view of the explanation having been made above, it is possible to solve the problem that blood flow cannot be properly measured due to artifact noises. Accordingly, blood flow can be measured by applying the laser blood-flow meter 10 to a monitor system which is necessary to receive for a long time blood flow data and biological data having correlation with the blood flow. In addition, it is possible to readily and stably measure blood flow in a head and quarters independently of each other.

Since the laser blood-flow meter 10 is designed to have the first light-reflector 14 for turning the laser beams L irradiated from the laser-beam irradiator 12 to the biological structure 11, and the second light-reflector 16 for turning the scattered beams S coming from the biological structure 11 to the semispherical lens 15, it is possible to efficiently collect the scattered beams S through the semispherical lens 15.

In addition, since the laser blood-flow meter 10 is designed to have the beam-block 19 which prevents the laser beams L having passed through the glass plate 18 from reaching the second light-reflector 16 and the semispherical lens 15 without reaching the biological structure 11, it is possible to remove the laser beams reflecting at a surface of the biological structure 11 without entering the biological structure 11, and collect only the scattered beams S returning back from the biological structure 11, through the semispherical lens 15, ensuring no necessity of measuring unnecessary signals.

The laser blood-flow meter 10 can monitor not only blood flow, but also operation of a heart, a pulsating flow, and operation of a blood vessel, and, based on monitoring of them, further monitor physiological function such as autonomic nervous system and central nervous system.

The laser blood-flow meter 10 in accordance with the first embodiment can measure blood flow in semispherical biological structure having a diameter of 2 to 4 millimeters both inclusive, for instance.

The sensor unit 110 may be mounted in a mobile communication terminal such as a mobile phone or PHS, in which case, the detection signals are transmitted to the controller through radio-signals.

Though the beam-block 19 is designed to be compressed onto a surface of the biological structure 11 in the first embodiment, the beam-block 19 may be designed to be inserted into the blood vessel area 11a in the biological structure 11, ensuring it possible to prevent detection of the scattered beams S resulted from the laser beams L not reaching the blood vessel area 11a, and accordingly, it would be possible to relatively increase the signal F(w) for properly measuring blood flow.

[Variant 1]

The laser blood-flow meter 10 in accordance with the above-mentioned first embodiment is of a backward-scattered type, and is designed to include a beam-collector comprised of the semispherical lens 15. A laser blood-flow meter in accordance with the first variant is designed not to include a beam-collector.

Though not illustrated, the laser blood-flow meter in accordance with the first variant has the same structure as that of the laser blood-flow meter 10 except that the laser blood-flow meter in accordance with the first variant does not include the semispherical lens 15.

Specifically, the laser blood-flow meter in accordance with the first variant includes a laser-beam irradiator 12 for irradiating laser beams to biological structure, a detector 13 for detecting scattered beams resulted from backward-scattering of the laser beams in the biological structure, a light-guide or a pin-hole 17 for guiding the scattered beams to the detector 13, and a case 110a in which the laser-beam irradiator 12, the light-guide 17 and the detector 13 are arranged. The case 110a has a flat contact-surface 101, as at least a part of an external surface of the case 110a, at which the case 110a makes contact with a surface of the biological structure 11 when blood flow of the biological structure 11 is measured. The laser-beam irradiator 12, the light-guide 17 and the detector 13 are arranged in this order on a path substantially parallel with the flat contact-surface 101. The laser blood-flow meter measures blood flow of the biological structure 11 in accordance with the scattered beams detected by the detector 13.

The laser blood-flow meter in accordance with the first variant is designed to include the case 110a in which the laser-beam irradiator 12, the first and second light-reflectors 14 and 16, the semispherical lens 15, the light-guide 17, and the detector 13 are arranged. The case 110a is designed to have a flat contact-surface 101 as at least a part of an external surface of the case 110a. The case 110a makes contact with a surface of the biological structure 11 through the flat contact-surface 101 when blood flow of the biological structure 11 is measured. In addition, the laser-beam irradiator 12, the semispherical lens 15, the light-guide 17 and the detector 13 are arranged in this order on a linear path substantially parallel with the flat contact-surface 101. Hence, it is possible to make the contact-surface 101 broader and more stable without increasing a size of the sensor unit 110. Thus, the sensor unit 110 can be readily attached to a target, and be less influenced by noises caused by oscillation.

Since the laser blood-flow meter in accordance with the first variant does not include the semispherical lens 15 as a light-guide, the laser blood-flow meter could have a smaller beam-collection efficiency than the laser blood-flow meter 10. However, the laser blood-flow meter in accordance with the first variant can introduce the scattered beams S returning back from the biological structure 11 to the detector 13 through the second light-reflector 16 and the light-guide 17, similarly to the laser blood-flow meter 10.

Second Embodiment

Figure 5:
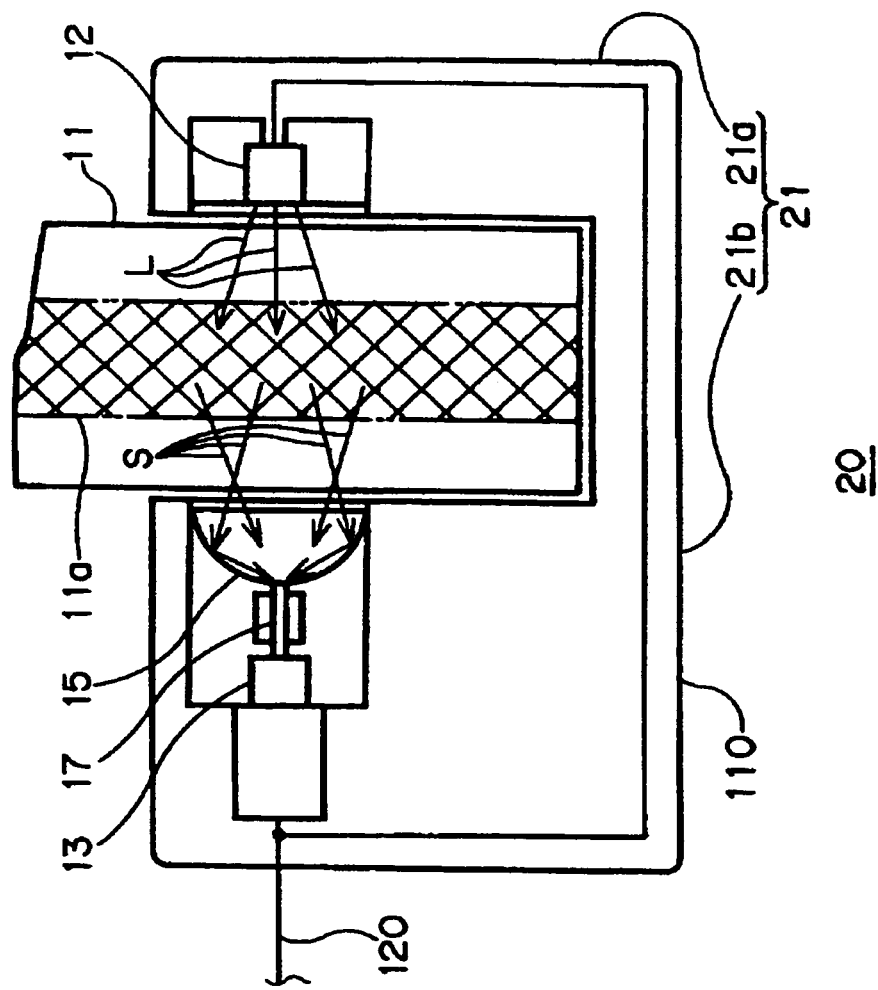
FIG. 5 is a cross-sectional view of the laser blood-flow meter in accordance with the second embodiment of the present invention.
Figure 6:
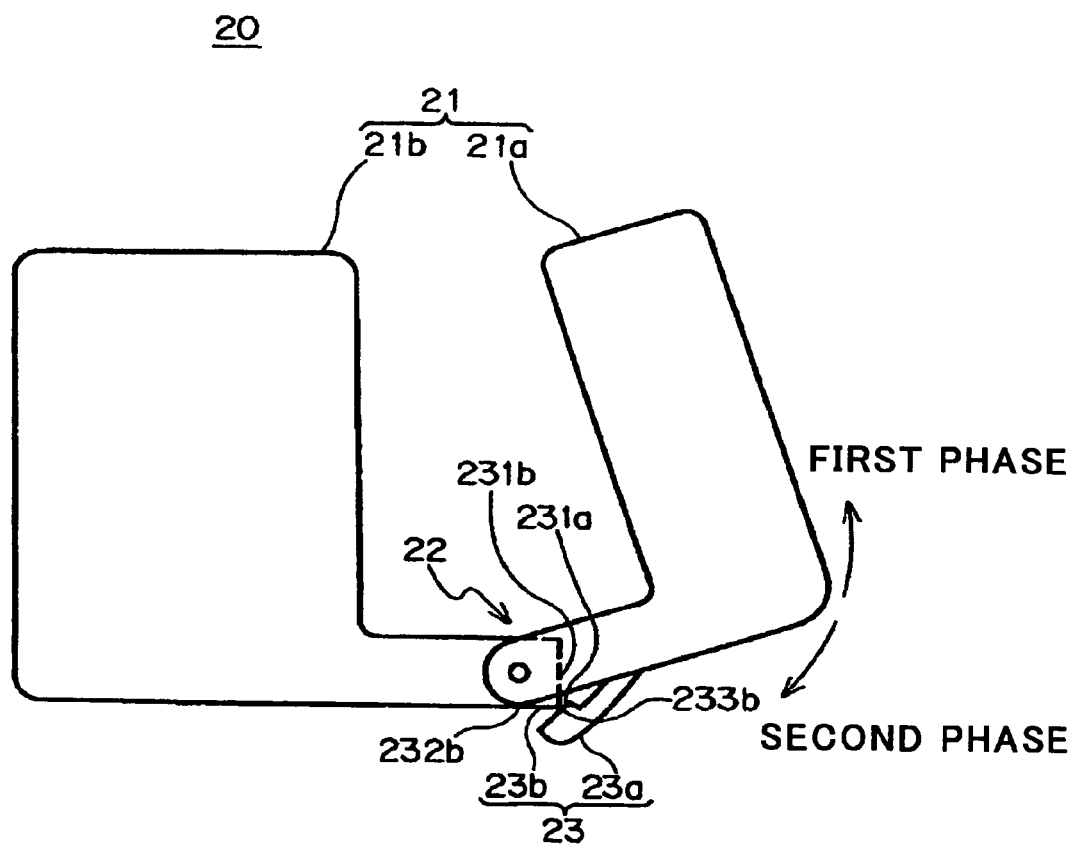
FIG. 6 is a front view of the laser blood-flow meter in accordance with the second embodiment of the present invention.

FIGS. 5 and 6 illustrate a laser blood-flow meter 20 in accordance with the second embodiment.

Since the laser blood-flow meter 20 is structurally identical with the laser blood-flow meter 10 except a later-mentioned difference, parts or elements that correspond to the laser blood-flow meter 10 have been provided with the same reference numerals, and are not explained.

As illustrated in FIG. 5, the detector 13 and the laser-beam irradiator 12 in the laser blood-flow meter 20 are disposed on opposite sides to each other relative to the biological structure 11 such that the detector 13 detects forward-scattered beams S. That is, the laser blood-flow meter 20 in accordance with the second embodiment is of a forward-scattered type meter.

Unlike the laser blood-flow meter 10 in accordance with the first embodiment, the laser blood-flow meter 20 is not necessary to include the first and second light-reflectors 14 and 16, and the beam-block 19.

The laser blood-flow meter 20 is designed to include a clip 20 for sandwiching biological structure therein. The clip 21 is comprised of a first portion 21a in which the laser-beam irradiator 12 is arranged, and a second portion 21b in which the semispherical lens 15, the light-guide 17, and the detector 13 are arranged.

As illustrated in FIG. 6, the first and second portions 21a and 21b are connected to each other through a hinge 22 such that they are rotatable to each other. By rotating the first and/or second portions 21a and 21b around the hinge 22, the first and second portions 21a and 21b come close to each other or go away from each other.

The hinge 22 may be a separate part independently of the first and second portions 21a and 21b, or may be a part of the first and/or second portions 21a and 21b.

The laser blood-flow meter 20 further includes a phase-converter 23 providing a first phase in which the first and second portions 21a and 21b sandwich the biological structure 11 therebetween such that the laser blood-flow meter 20 is attached to the biological structure 11, and a second phase in which the first and second portions 21a and 21b are open to each other such that the laser blood-flow meter 20 is released from the biological structure 11.

The phase-converter 23 is comprised of an elastic hook 23a, and a fixed portion 23b to which the elastic hook 23a is engaged. The elastic hook 23a extends beyond the first portion 21a, and the fixed portion 23b is formed as a part of the second portion 21b.

When the first and second portions 21a and 21b move from the first phase to the second phase or vice versa, positional relation between the fixed portion 23b and a planar portion 231a of the elastic hook 23a varies. Specifically, the planar portion 231a of the elastic hook 23a engages to a first planar portion 231b of the fixed portion 23b in the first phase, a second planar portion 232b of the fixed portion 23b in the second phase, and a corner 233b of the fixed portion 23b between the first and second phases.

In the first phase, the planar portion 231a of the elastic hook 23a engages to the first planar portion 231b of the fixed portion 23b, and in the second phase, the planar portion 231a of the elastic hook 23a engages to the second planar portion 232b of the fixed portion 23b. Hence, the elastic hook 23a and the fixed portion 23b are in a stable condition in the first and second phases.

In particular, in the first phase, the first and second portions 21a and 21b sandwich the biological structure such as an ear lobe therebetween. Hence, the sensor unit 110 can be kept hung from the biological structure 11.

The corner 233b to which the elastic hook 23a engages between the first and second phases is located remoter from a rotation axis of the hinge 22 than the first and second planar portions 231b and 232b. Accordingly, elastic deformation of the elastic hook 23a observed between the first and second phases is greater than the same observed in the first or second phase. This means that the first and second portions 21a and 21b are in an instable condition between the first and second phases, and hence, the first and second portions 21a and 21b are likely to transfer to the first or second phase.

Since the laser blood-flow meter 20 in accordance with the second embodiment is designed to have the clip 20 for enabling the laser blood-flow meter 20 to be attached to the biological structure 11, the laser blood-flow meter 20 can be used in a condition in which the laser blood-flow meter 20 is attached to the biological structure 11.

In accordance with the laser blood-flow meter 20, it is possible to measure blood flow in a cylindrical biological structure having a radius in the range of about 1 to 3 millimeters both inclusive, if the biological structure has a thickness in the range of 1 to 6 millimeters both inclusive.

By dividing the measured blood flow by a volume of biological structure through which the laser beams L pass, it is possible to absolutize blood flow, whereas absolutization of blood flow was impossible in a conventional forward-scattered type laser blood-flow meter. Absolutized blood flow has a unit of milliliter/min/mm$^3$, for instance.

[Variant 2]

The laser blood-flow meter 20 in accordance with the above-mentioned second embodiment is of a forward-scattered type, and is designed to include a beam-collector comprised of the semispherical lens 15. A laser blood-flow meter in accordance with the second variant is designed not to include a beam-collector.

Though not illustrated, the laser blood-flow meter in accordance with the second variant has the same structure as that of the laser blood-flow meter 20 except that the laser blood-flow meter in accordance with the second variant does not include the semispherical lens 15.

Specifically, the laser blood-flow meter in accordance with the second variant includes a laser-beam irradiator 12 for irradiating laser beams to biological structure, and a detector 13 for detecting scattered beams resulted from scattering of the laser beams in the biological structure. The detector 13 and the laser-beam irradiator 12 are disposed on opposite sides to each other relative to the biological structure 11 such that the detector 13 detects forward-scattered beams. The laser blood-flow meter measures blood flow of the biological structure in accordance with the scattered beams detected by the detector 13.

In the above-mentioned first and second embodiments, the laser blood-flow meters 10 and 20 include the semispherical lens 15 as a beam-collector. It should be noted that a beam-collector is not to be limited to the semispherical lens 15, but may be comprised of any optical element such as a dome-type or convex lens, if it can collect laser beams.

Furthermore, in the above-mentioned first and second embodiments and their variants, any optical element may be used in place of the pin-hole 17, if it can guide laser beams to the detector 13. For instance, an optical fiber or a bar lens may be used.

Third Embodiment

The third embodiment relates to a system for monitoring bio-data.

Figure 7:
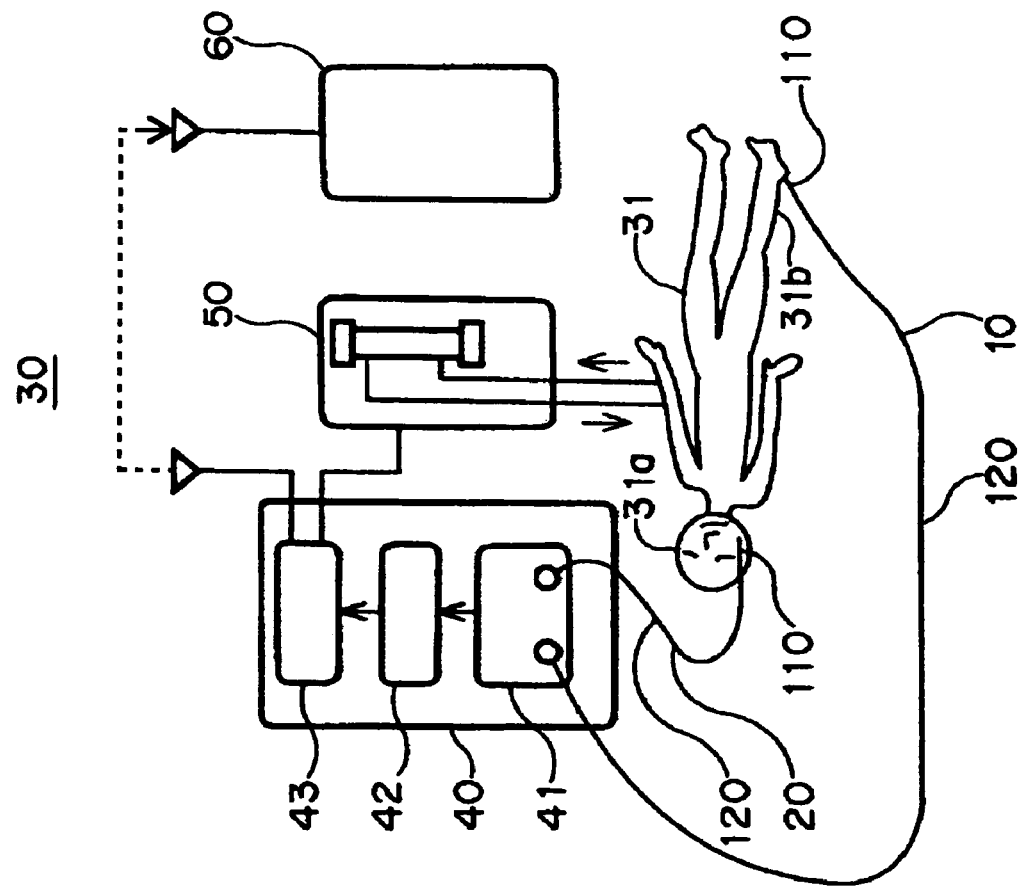
FIG. 7 illustrates a system for monitoring bio-data, in accordance with the third embodiment of the present invention.

As illustrated in FIG. 7, a bio-data monitoring system 30 in accordance with the third embodiment of the present invention includes the laser blood-flow meter 20 for measuring blood flow of a head 31a (for instance, an ear lobe) of a man 31, and the laser blood-flow meter 10 for measuring blood flow in any one of quarters of the man 31, for instance, a leg 31b. The system 30 monitors bio-data of the man 31, based on the measured blood flow in the head 31a and the leg 31b.

The laser blood-flow meters 10 and 20 are controlled commonly by a controller 40.

The controller 40 is comprised of an input section 41 which receives detection signals transmitted from the sensor units 110 of the laser blood-flow meters 10 and 20, and converts the received analog detection signals into digital signals, a calculator 42 which calculates blood flow of the man 31, based on the digital detection signals, and an output section 43 which outputs data indicative of the blood flow calculated by the calculator 42.

The calculator 42 is comprised of a central processing unit (CPU), a digital signal processor (DSP), a personal digital assistant (PDA) or a personal computer (PC), for instance, and carries out various judgments mentioned later and annunciation control as well as calculation of blood flow and control of an operation of the laser-beam irradiator 12.

The bio-data monitoring system 30 monitors bio-data, simultaneously circulating blood between the man 31 and an external device. For instance, the system 30 includes an artificial dialysis device 50 for carrying out artificial dialysis to the man 31 as well as monitoring bio-data of the man 31.

The system 30 is designed to further include a monitor display 60 for monitoring blood flow data calculated by the calculator 42.

The output section 43 of the controller 40 transmits data to the artificial dialysis device 50 and the monitor display 60 through wires or through radio-signals.

If not influenced by artifact noises, blood flow of the head 31a and blood flow of any one of quarters of the man 31 are in synchronization with each other. Similarly, if not influenced by artifact noises, a blood-flow waveform of the head 31a and a blood-flow waveform of any one of quarters of the man 31 are in synchronization with each other.

Thus, the calculator 42 judges whether blood flow and a blood-flow waveform of the head 31a such as an ear lobe and those of any one of the quarters such as the leg 31b are in synchronization with each other, respectively. The calculator 42 does not use blood flow and a blood-flow waveform measured while the above-mentioned blood flows and blood-flow waveforms are judged not to be in synchronization with each other, for monitoring bio-data of the man 31.

Figures 8A, 8B:
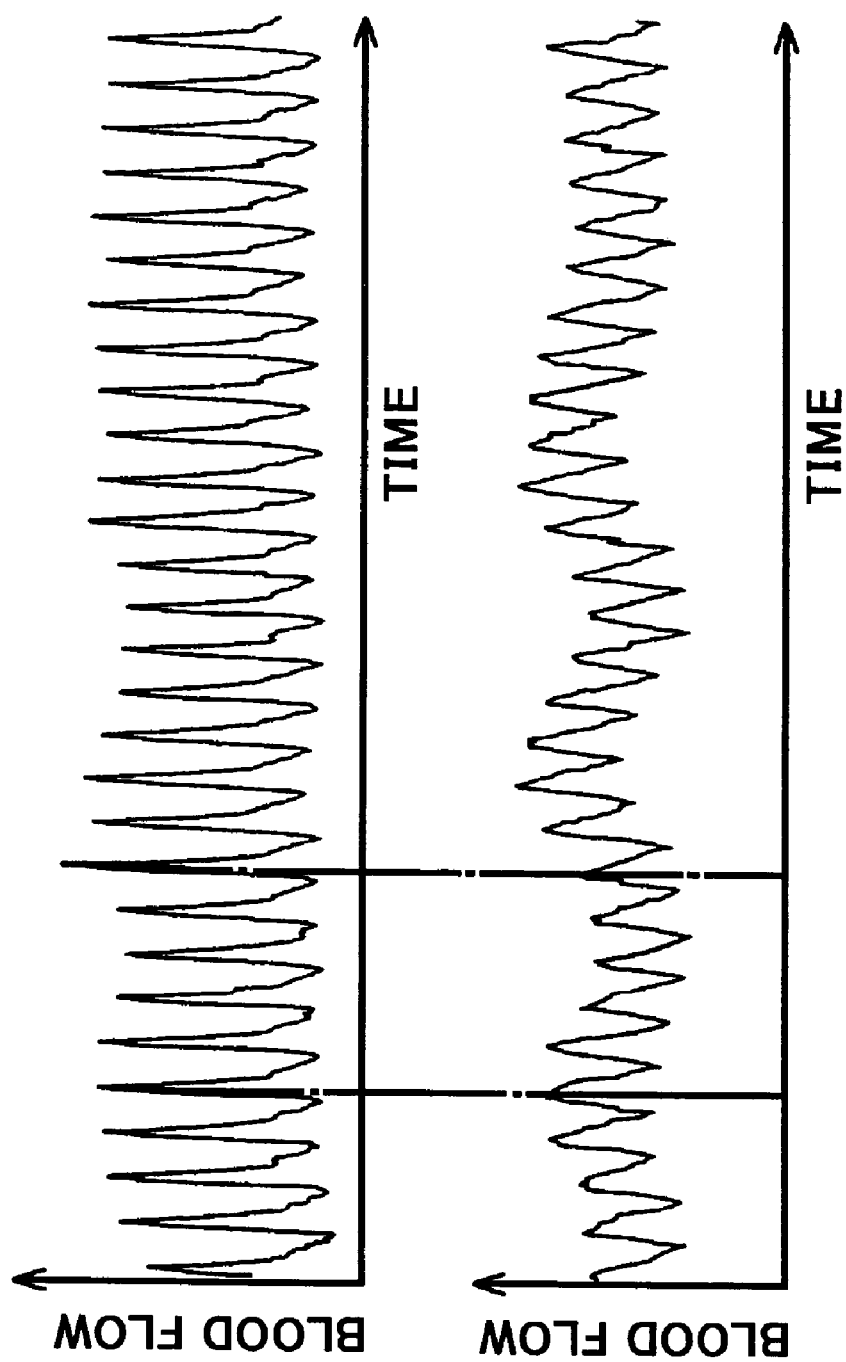
FIGS. 8A and 8B illustrate blood-flow waveforms in synchronization with each other.

Each of FIGS. 8A and 9A illustrates blood flow of the leg 31b and a waveform of the blood flow, and each of FIGS. 8B and 9B illustrates blood flow of the head 31a such an ear lobe and a waveform of the blood flow. The blood flows and its waveforms illustrated in FIGS. 8A and 8B are measured by the laser blood-flow meters 10 and 20, and the blood flows and its waveforms illustrated in FIGS. 9A and 9B are measured by a conventional laser blood-flow meter.

Comparing FIGS. 8A and 8B to each other, the blood-flow waveforms are almost in synchronization with each other every certain period, and magnitudes of the blood flow are almost in synchronization with each other.

When the blood flow of the leg 31b and its waveform as illustrated in FIG. 8A are in synchronization with the blood flow of the head 31a (specifically, an ear lobe) and its waveform as illustrated in FIG. 8B, they are used for monitoring bio-data of the man 31.

In contrast, comparing FIGS. 9A and 9B to each other, the blood-flow waveforms in FIGS. 9A and 9B are different from each other for every certain period, and magnitudes of the blood flows in FIGS. 9A and 9B are different from each other. Specifically, the blood flows and their waveforms in FIGS. 9A and 9B are not in synchronization with each other.

When the blood flow of the leg 31b and its waveform as illustrated in FIG. 9A are not in synchronization with the blood flow of the head 31a (specifically, an ear lobe) and its waveform as illustrated in FIG. 9B, they are not used for monitoring bio-data of the man 31.

In the above-mentioned way, the calculator 42 removes blood flow and its waveform unusable for monitoring bio-data of the man 31, and selects only blood flow and its waveform usable for doing the same.

A waveform of blood flow is inherent to an individual. Hence, the calculator 42 compares a blood-flow waveform to a standard waveform having been stored for each of individuals to thereby judge whether a blood-flow waveform was properly measured. If the calculator 42 judges that a blood-flow waveform is not properly measured, the calculator 42 does not use the blood-flow waveform for monitoring bio-data of the man 31. Thus, accuracy in judgment is enhanced.

The calculator 42 is designed to judge whether the man 31 is in a serious condition.

Up and down of blood flow is in synchronization with up and down of a blood pressure. Based on this fact, the calculator 42 continuously or periodically compares an average of blood flow to measured blood flow to thereby judge whether the man 31 is in a serious condition. Specifically, if measured blood flow is higher or lower than the average by a predetermined degree or more, the calculator 42 judges that the man 31 is in a serious condition.

Reduction in a blood pressure is accompanied with reduction in an amplitude of a blood-flow waveform. Hence, the calculator 42 can judge whether the man 31 is in a serious condition by continuously or periodically comparing an amplitude of a predetermined blood-flow waveform to an amplitude of a real-time measured blood-flow waveform.

The calculator 42 may judge whether the man 31 is in a serious condition, based on both of blood-flow and an amplitude of a blood-flow waveform, or based on one of them.

For instance, a pattern of blood flow and a pattern of an amplitude of a blood-flow waveform both observed in a certain dialysis patient when a certain period of time in the range of 30 minutes to an hour has passed after starting dialysis are recorded as standards. The calculator 42 may judge whether the man 31 is in a serious condition, based on reduction in blood flow relative to the standards, reduction in an amplitude of a blood-flow waveform relative to the standards, and an increase in a heartbeat number which can be read out of the blood-flow waveform.

For instance, the calculator 42 may alarm when a product F×S reduces by a predetermined degree relative to a predetermined standard of the product, wherein F indicates reduction in an amplitude of a blood-flow waveform, and S indicates 1/T wherein T indicates a heartbeat number.

For instance, if the product reduces by 10%, the calculator 42 judges that the man 31 is in a condition in which small attention has to be paid to a patient, and transmits a first level alarm. If the product reduces by 20%, the calculator 42 judges that the man 31 is in a condition in which normal attention has to be paid to a patient, and transmits a second level alarm. If the product reduces by 30%, the calculator 42 judges that the man 31 is in a dangerous condition, and transmits a third level alarm. If the product reduces by 40%, the calculator 42 judges that the man 31 is in a serious condition, and transmits a top level alarm.

In place of the calculator 42, the controller 40, the artificial dialysis device 50 or the monitor display 60 may alarm.

Since the system in accordance with the third embodiment has the laser blood-flow meters 10 and 20 in accordance with the first and second embodiments, it is possible to continuously measure blood flow of the head 31*a* and the leg 31*b* of the man 31 stably and independently of each other by attaching the sensor units 110 of the laser blood-flow meters 10 and 20 to the man 31 with reduced influences by artifact noises.

In addition, the calculator 42 judges whether blood flow and a blood-flow waveform of the head 31*a* such as an ear lobe and those of any one of the quarters such as the leg 31*b* are in synchronization with each other, respectively. The calculator 42 does not use blood flow and a blood-flow waveform measured while the above-mentioned blood flows and blood-flow waveforms are judged not to be in synchronization with each other, for monitoring bio-data of the man 31. Thus, bio-data of the man 31 is monitored based on blood flow and a blood-flow waveform both properly measured. In other words, since blood flows and blood-flow waveforms which are not in synchronization with each other, respectively, due to artifact noises are not used for monitoring bio-data, obtained bio-data is less influenced by artifact noises.

Furthermore, the calculator 42 is designed to compare measured blood flow and blood-flow waveform to standard blood flow and blood-flow waveform having been stored in advance to thereby judge whether the man 31 is in a serious condition, and if the man 31 is judged to be in a serious condition, the calculator 42 makes annunciation. Thus, a user of the system 30 can soon become aware that the man 31 is in a serious condition.

Bio-data of a man has been conventionally monitored through the use of a non-direct type hemadynamometer. Though the use of a non-direct type hemadynamometer is non-invasive similarly to the system 30, a non-direct type hemadynamometer cannot continuously monitor bio-data unlike the system 30 in accordance with the third embodiment.

A pulse-wave meter or a pulse oxi-meter has been conventionally used for continuously monitoring bio-data. However, a pulse-wave meter and a pulse oxi-meter are too late to respond to sudden change in blood circulation, and cannot clearly show variance in an amplitude of waveforms. Hence, they are merely assistants to a hemadynamometer.

In contrast, since the system 30 can monitor bio-data of the man 31 in non-invasive manner by using the laser blood-flow meters 10 and 20, almost no burden is exerted on a patient. In addition, it is possible to continuously monitor bio-data, and hence, it is also possible to swiftly and surely judge that the man 31 is in a serious condition. Thus, the system 30 in accordance with the third embodiment can have a higher rate and higher accuracy at which the system 30 judges whether the man 31 is in a serious condition, than the conventional ways.

The system 30 in accordance with the third embodiment may be designed to transmits command signals to the artificial dialysis device 50 for controlling a volume of deicing and/or a dialysis temperature, and further for giving an alarm to a user to urge to do so. Furthermore, the system 30 may be designed to estimate dynamics of circulator organs to which dialysis is being carried out.

Though the system 30 is designed to include the artificial dialysis device 50, the system 30 may be designed to include other external device(s) for making circulation between itself and the man 31. For instance, the system 30 may be designed to include a blood transfusion device.

As an alternative, the system 30 may be designed not to include the artificial dialysis device 50 or other external device(s). The system 30 may be designed to simply include the controller 40 and the sensor units 110 (that is, the laser blood-flow meters 10 and 20).

The system 30 in accordance with the third embodiment can monitor not only blood flow, but also operation of a heart, a pulsating flow, and operation of a blood vessel, and, based on monitoring of them, further monitor physiological function such as autonomic nervous system and central nervous system. For instance, the system 30 is applicable to administration of athletes, space medicine, monitoring of development of neonates, diagnosis of children, judgment as to when medicine becomes efficacious, animal experiments, and other uses.

In the system 30 in accordance with the third embodiment, the laser blood-flow meter 20 in accordance with the second embodiment is used for measuring blood flow of the head 31*a*. The laser blood-flow meter 10 in accordance with the first embodiment may be used in place of the laser blood-flow meter 20, in which case, an aid for readily attaching the laser blood-flow meter 10 to the head 31a, such as a head band, a head phone or a cap, may be integral with the laser blood-flow meter 10. With such an aid, the laser blood-flow meter 10 can be readily attached to and released from the head 31a.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

The entire disclosure of Japanese Patent Application No. 2003-156943 filed on Jun. 2, 2003 including specification, claims, drawings and summary is incorporated herein by reference in its entirety.

What is claimed is:

1. A laser blood-flow meter comprising:
   a laser-beam irradiator for irradiating laser beams to a biological structure;
   a detector for detecting scattered beams resulted from scattering of said laser beams in said biological structure, said laser blood-flow meter measuring blood flow of said biological structure in accordance with said scattered beams detected by said detector;
   a beam-collector for collecting said scattered beams to direct the collected beams to said detector; and
   a light-guide arranged between said detector and said beam-collector for guiding beams collected by said beam-collector to said detector;
   a case in which said laser-beam irradiator, said beam-collector and said detector are arranged;
   a first beam-turner for turning said laser beams irradiated from said laser-beam irradiator towards said biological structure; and
   a second beam-turner for turning said scattered beams towards said beam-collector,
   wherein said detector and said laser-beam irradiator are disposed on a common side relative to said biological structure such that said detector detects backward-scattered beams,
   wherein said case comprises a flat contact-surface, as at least a part of an external surface thereof, at which said case makes contact with a surface of said biological structure when blood flow of said biological structure is measured,
   wherein said laser-beam irradiator, said beam-collector and said detector are arranged in order on a path substantially parallel with said flat contact-surface,
   wherein said contact-surface comprises a beam-transmissive portion through which said laser beams can transmit, and
   wherein said laser blood-flow meter further comprises a beam-block which prevents laser beams having passed through said beam transmissive portion from being directed towards said second beam-turner and said beam-collector with reaching said biological structure.

2. The laser blood-flow meter as set forth in claim 1, wherein said detector and said laser-beam irradiator are disposed on opposite sides to each other relative to said biological structure such that said detector detects forward-scattered beams.

3. The laser blood-flow meter as set forth in claim 1, wherein said beam-collector is comprised of a semispherical lens.

4. The laser blood-flow meter as set forth in claim 1, wherein said light-guide is comprised of one of a pin-hole, an optic fiber and a bar lens.

5. The laser blood-flow meter as set forth in claim 1, wherein said beam-block projects outwardly over said beam-transmissive portion.

6. A laser blood-flow meter comprising:
   a laser-beam irradiator for irradiating laser beams to a biological structure;
   a detector for detecting scattered beams resulted from backward-scattering of said laser beams in said biological structure, said laser blood-flow meter measuring blood flow of said biological structure in accordance with said scattered beams detected by said detector;
   a light-guide for guiding said scattered beams to said detector;
   a case in which said laser-beam irradiator, said light-guide and said detector are arranged;
   a first beam-turner for turning said laser beams irradiated from said laser-beam irradiator towards said biological structure; and
   a second beam-turner for turning said scattered beams towards said light-guide,
   wherein said case comprises a flat contact-surface, as at least a part of an external surface thereof, at which said case makes contact with a surface of said biological structure when blood flow of said biological structure is measured, and
   wherein said laser-beam irradiator, said light-guide and said detector are arranged in order on a path substantially parallel with said flat contact-surfaces,
   wherein said contact-surface comprises a beam-transmissive portion through which said laser beams can transmit, and
   wherein said laser blood-flow meter further comprises a beam-block which prevents laser beams having passed through said beam-transmissive portion from being directed towards said second beam-turner and said light-guide without reaching said biological structure.

7. The laser blood-flow meter as set forth in claim 6, wherein said light-guide is comprised of one of a pin-hole, an optic fiber and a bar lens.

8. The laser blood-flow meter as set forth in claim 6, wherein said beam-block projects outwardly over said beam-transmissive portion.

9. A system for monitoring bio-data of a biological structure, including a laser blood-flow meter measuring blood flow of said biological structure in accordance with scattered beams resulted from scattering of laser beams in said biological structure which laser beams have been irradiated to said biological structure, said system monitoring said bio-data, based on blood flow in a head of said biological structure and blood flow in any one of quarters of said biological structure,
   said system including a controller which judges whether a blood flow and a blood-flow waveform of a said head of said biological structure are in synchronization with a blood flow and a blood-flow waveform of said any one of quarters of said biological structure, and does not use a blood flow and a blood-flow waveform obtained when said blood flow and said blood-flow waveform of said head is not in synchronization with said blood flow and said blood-flow waveform of said any one of quarters, for monitoring said bio-data,
   wherein said laser blood-flow meter comprises:
   a laser-beam irradiator for irradiating said laser beams to said biological structure;

a detector for detecting said scattered beams resulted from said scattering of said laser beams in said biological structure;

a beam-collector for collecting said scattered beams to direct the collected beams to said detector; and a light-guide arranged between said detector and said beam-collector for guiding beams collected by said beam-collector to said detector;

a case in which said laser-beam irradiator, said beam-collector and said detector are arranged;

a first beam-turner for turning said laser beams irradiated from said laser-beam irradiator towards said biological structure; and a second beam-turner for turning said scattered beams towards said beam-collector, wherein said detector and said laser-beam irradiator are disposed on a common side relative to said biological structure such that said detector detects backward-scattered beams, wherein said case comprises a flat contact-surface, as at least a part of an external surface thereof, at which said case makes contact with a surface of said biological structure when blood flow of said biological structure is measured, wherein said laser-beam irradiator, said beam-collector and said detector are arranged in order on a path substantially parallel with said flat contact-surface, wherein said contact-surface comprises a beam-transmissive portion through which said laser beams can transmit, and wherein said laser blood-flow meter further comprises a beam-block which prevents laser beams having passed through said beam transmissive portion from being directed towards said second beam-turner and said beam-collector with reaching said biological structure.

10. The system as set forth in claim 9, wherein said controller compares the measured blood flow and blood-flow waveform to a reference blood flow and a reference blood-flow waveform, respectively, to judge whether said measured blood flow and blood-flow waveform are properly measured, and wherein a blood flow and a blood-flow waveform having been judged not to be properly measured are not used for monitoring said bio-data.

11. The system as set forth in claim 9, wherein said controller judges whether a person to be monitored is in a serious condition.

12. The system as set forth in claim 11, wherein said controller compares the measured blood flow and blood-flow waveform to a reference blood flow and a reference blood-flow waveform, respectively, to judge whether a person to be monitored is in a serious condition.

13. The system as set forth in claim 11, further comprising an annunciator which makes annunciation when said controller judges that said person is in a serious condition.

14. The system as set forth in claim 9, wherein said system monitors said bio-data while blood is circulated between a person and an external device.

15. The system as set forth in claim 9, further comprising an artificial dialysis device for carrying out artificial dialysis, and wherein said system monitors said bio-data of a person while dialysis is carried out to said person by said artificial dialysis device.

* * * * *